US00PP35114P2

(12) United States Plant Patent
Kleinwee

(10) Patent No.: US PP35,114 P2
(45) Date of Patent: Apr. 18, 2023

(54) ***PETUNIA* PLANT NAMED 'PEHY0076'**

(50) Latin Name: *Petunia hybrida*
Varietal Denomination: PEHY0076

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/973,637

(22) Filed: Oct. 26, 2022

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.1, 356.13
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0076' particularly distinguished by its small sized, red-purple with white flowers, medium to late flowering and a mounding plant habit.

1 Drawing Sheet

Latin name of the genus and species of the plant claimed: *Petunia hybrida.*

Varietal denomination: 'PEHY0076'.

BACKGROUND OF THE NEW PLANT

The present invention comprises a new *Petunia*, botanically known as *Petunia hybrida*, and hereinafter referred to by the variety name 'PEHY0076'.

'PEHY0076' is a product of a planned breeding program. The new cultivar has small sized, red-purple with white flowers, medium to late flowering and a mounding plant habit.

'PEHY0076' originated from a mutation treatment by x-rays on unrooted cuttings in a controlled laboratory environment in Enkhuizen, The Netherlands in June 2018. The source variety was the variety 'PEHY0044' (U.S. Plant Pat. No. 32,368). Compared to 'PEHY0044', 'PEHY0076' has a red purple with white flower color while 'PEHY0044' has a purple with white color. Also, 'PEHY0076' has relatively bigger white sections than 'PEHY0044' when grown under the same conditions.

The resulting plants were planted in July 2018. 'PEHY0076' was selected as flowering plant in December 2018 in a controlled environment in Enkhuizen, The Netherlands.

The first act of asexual reproduction of 'PEHY0076' was accomplished when vegetative stem cuttings were propagated from the initial selection in January 2019 in a controlled environment in Enkhuizen, The Netherlands.

BRIEF SUMMARY OF INVENTION

Horticultural examination of plants grown from cuttings of the plant initiated in January 2019 and continuing thereafter, has demonstrated that the combination of characteristics as herein disclosed for 'PEHY0076' are firmly fixed and are retained through successive generations of asexual reproduction.

'PEHY0076' has not been observed under all possible environmental conditions. The phenotype may vary significantly with variations in environment such as temperature, light intensity, and day length.

A Plant Breeder's Right for this cultivar has not yet been applied for. 'PEHY0076' has not been made publicly available prior to the effective filing date of this application, notwithstanding any disclosure that may have been made less than one year prior to the effective filing date of this application by the inventor or another who obtained 'PEHY0076' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0076' with colors being as true as possible with an illustration of this type.

Figure 1:
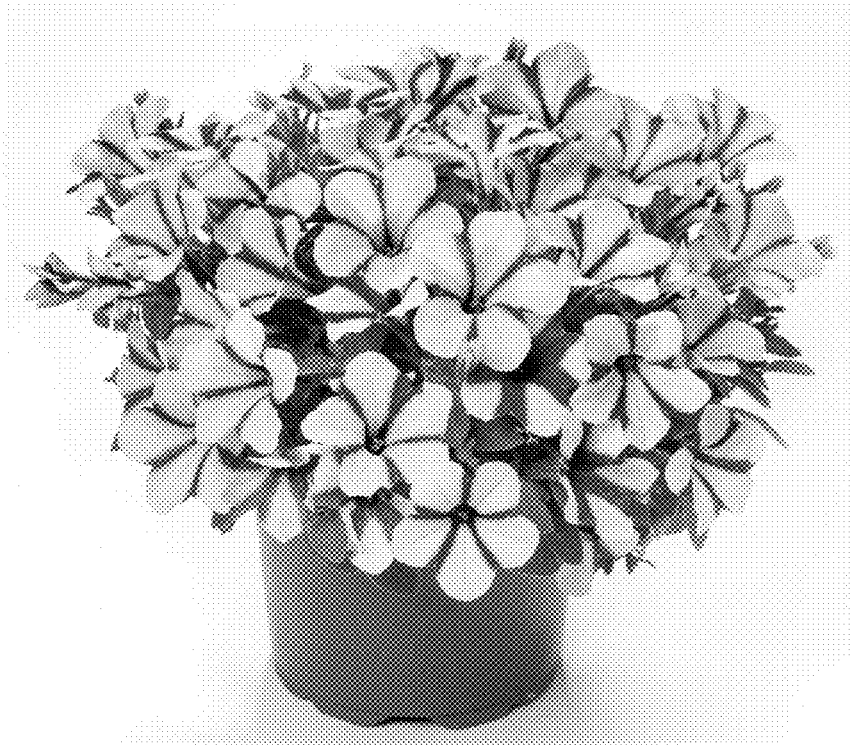
Figure 2:
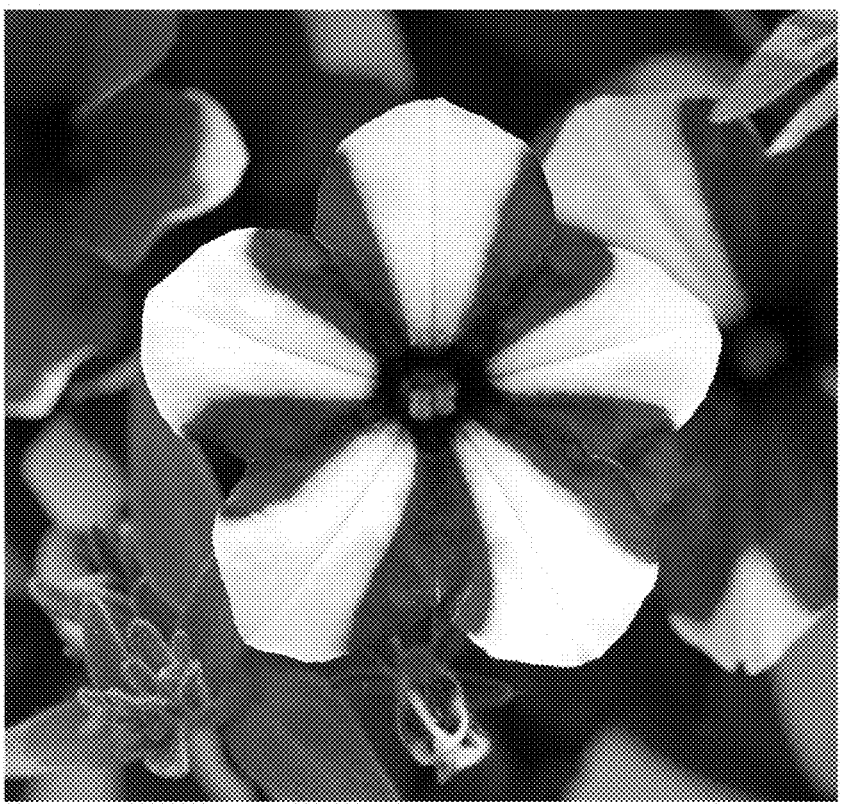

The photographic drawings show in FIG. 1 a flowering plant of the new variety and in FIG. 2 a close-up of the flower.

DETAILED BOTANICAL DESCRIPTION

The aforementioned photograph of the potted plant were taken in April 2021 from plants growing indoor in 12 cm pots in Andijk, The Netherlands. The close up was taken from the same plants in May 2021. These plants were approximately 11 weeks and 15 weeks of age, respectively.

The plant descriptions and measurements were taken in September 2022 in Andijk, The Netherlands on approximately 20 week old plants that were growing in containers.

Color references are made to The Royal Horticultural Society Colour Chart (R.H.S.) 2001.

TABLE 1

DIFFERENCES BETWEEN THE NEW VARIETY 'PEHY0076' AND A SIMILAR VARIETY

| | 'PEHY0076' | 'Littletuniabic. Illusion' (Not patented) |
|---|---|---|
| Plant habit: | Mounding | Mounding to upright |
| Flower size: | Small | Very small |
| Area secondary color (white) vs primary color: | Relatively large | Relatively low |

Plant:
- *Form, growth and habit.*—Mounding plant habit.
- *Plant height.*—29 cm.
- *Plant height (inflorescence included).*—31 cm.
- *Plant diameter (width).*—Approximately 35 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 137B.
- *Immature leaf, color lower surface.*—RHS 147B.
- *Mature leaf, color upper surface.*—RHS 137A.
- *Mature leaf, color lower surface.*—RHS 147B.
- *Length.*—2.3-4.0 cm.
- *Width.*—1-1.7 cm.
- *Shape.*—Ovate.
- *Base shape.*—Shortly Attenuate.
- *Apex shape.*—Acute.
- *Margin.*—Entire.
- *Texture, upper surface.*—Densely covered with short hair.
- *Lower surface.*—Densely covered with short hairs.
- *Color of veins, upper surface.*—RHS 146D.
- *Color of veins, lower surface.*—RHS 146D.
- *Petiole color.*—RHS 146D.
- *Length.*—0.4 cm.
- *Diameter.*—0.2 cm.
- *Petiole texture.*—Densely covered with short hairs.

Stem:
- *Quantity of main branches per plant.*—4-5.
- *Color of stem.*—RHS 146D.
- *Length of stem.*—23 cm.
- *Diameter.*—0.3 cm.
- *Length of internodes.*—1.5-2.5 cm.
- *Texture.*—Dense, mostly glandular short hairs.
- *Color of pedicel.*—RHS 146D.
- *Length of pedicel.*—1.0 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium to late flowering in greenhouse, flowering throughout the summer months.
- *Quantity of inflorescences per plant.*—Approximately 65.
- *Lastingness of individual blooms on the plant.*—About 7 days.
- *Fragrance.*—Rather strong smell.

Bud (just when opening):
- *Color.*—RHS 158A at top, stripes of RHS 11D with veins RHS 144B and stripes RHS 59A towards base.
- *Length.*—2.1 cm.
- *Width.*—0.4 cm.
- *Shape.*—Oblong.

Immature inflorescence:
- *Flower horizontal diameter.*—1.4 cm.
- *Color petals, upper surface.*—Stripes of RHS 59A, fading into RHS N66A at margin of stripe, with stripes RHS 158C and veins RHS 144D.
- *Color petals, lower surface.*—RHS N77A, with stripes RHS 158C and veins RHS 144B.

Mature flower:
- *Flower horizontal diameter.*—6 cm.
- *Flower height (vertical).*—2.5-3.5 cm.
- *Color upper surface.*—RHS N66A with stripes RHS 155A, and some spots RHS 9B near corolla tube.
- *Color lower surface.*—RHS N66A, with stripes RHS 155A.
- *Conspicuousness of veins.*—Medium.
- *Apex shape.*—Acuminate.
- *Margin.*—Entire.
- *Waviness of margin.*—Low.
- *Petal lobation.*—Medium.
- *Petal texture, upper surface.*—Smooth.
- *Petal texture, lower surface.*—Smooth, occasionally a short hair.
- *Corolla tube color outside.*—RHS 72C with veins RHS 187A.
- *Corolla tube color inside.*—RHS N77A with longitudinal stripes 187A.
- *Conspicuousness of veins in tube.*—Medium.
- *Corolla tube length.*—2 cm.
- *Corolla tube texture, outside.*—Rather dense and short glandular hairs.
- *Corolla tube texture, inside.*—Glabrous.

Calyx:
- *Color of sepal, upper surface.*—RHS 146A.
- *Color of sepal, lower surface.*—RHS 146A.
- *Length.*—1.0 cm.
- *Width.*—0.3 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.2 cm.
- *Style color.*—RHS 145C, some anthocyanin near style, RHS 187A.
- *Style length.*—1.5 cm.
- *Stigma color.*—RHS 145B.
- *Stamens.*—
- *Quantity per flower.*—5.
- *Color of filaments.*—RHS 145D.
- *Length filaments.*—1.2 cm.
- *Anther color.*—RHS 190B.
- *Anther length.*—0.2 cm.
- *Anther shape.*—Elliptical.
- *Color of pollen.*—RHS 190D.

*Pollen amount*.—Sparse.

*Fertility/seed set*.—Has not been observed on this hybrid.

*Disease/pest resistance*.—Has not been observed on this hybrid.

What is claimed is:

1. A new and distinct variety of *Petunia* plant named 'PEHY0076' substantially as illustrated and described herein.

* * * * *